(12) United States Patent
Lillis et al.

(10) Patent No.: US 7,020,562 B2
(45) Date of Patent: Mar. 28, 2006

(54) METHOD OF MONITORING THE OPERATION OF GAS SENSOR AND SYSTEM THEREFOR

(75) Inventors: Mark Lillis, South Windsor, CT (US); Spyros Nomikos, New Britain, CT (US); Dean Halter, West Hartford, CT (US)

(73) Assignee: Proton Energy Systems, Inc., Wallingford, CT (US)

( * ) Notice: Subject to any disclaimer, the term of this patent is extended or adjusted under 35 U.S.C. 154(b) by 61 days.

(21) Appl. No.: 10/249,313

(22) Filed: Mar. 31, 2003

(65) Prior Publication Data

US 2004/0193379 A1   Sep. 30, 2004

(51) Int. Cl.
*G06F 19/00* (2006.01)

(52) U.S. Cl. .................. 702/23; 73/19.04; 340/632

(58) Field of Classification Search ............ 702/22–25, 702/30–32, 45, 50, 55, 183, 188; 73/19.04, 73/19.05, 19.1, 23.24, 29.01; 340/501–502, 340/506, 511, 603, 606, 632; 429/90–93
See application file for complete search history.

(56) References Cited

U.S. PATENT DOCUMENTS

| | | | |
|---|---|---|---|
| 4,247,811 A * | 1/1981 | Findl .......................... 320/134 |
| 4,271,474 A * | 6/1981 | Belanger et al. .............. 702/24 |
| 4,594,297 A | 6/1986 | Polak et al. ................... 429/13 |
| 4,795,536 A | 1/1989 | Young et al. ................ 204/129 |
| 5,334,295 A * | 8/1994 | Gallagher et al. ........... 205/783 |
| 5,492,004 A * | 2/1996 | Berg et al. .................... 73/40.7 |
| 5,643,689 A | 7/1997 | Fleischer et al. ............. 429/33 |
| 5,724,255 A * | 3/1998 | Smith et al. ................. 700/266 |
| 5,741,611 A | 4/1998 | Fleischer et al. ........... 429/192 |
| 6,037,592 A * | 3/2000 | Sunshine et al. ........... 250/343 |
| 6,063,516 A * | 5/2000 | Grot et al. ..................... 429/22 |
| 6,106,968 A * | 8/2000 | Johnson et al. .............. 429/50 |
| 6,159,624 A | 12/2000 | Ozawa et al. ............... 428/689 |
| 6,251,243 B1 * | 6/2001 | Lindsay ...................... 204/400 |
| 6,290,594 B1 | 9/2001 | Osborne ....................... 454/75 |
| 6,337,009 B1 | 1/2002 | Nadanami et al. .......... 205/775 |
| 6,428,684 B1 * | 8/2002 | Warburton ................... 205/775 |
| 6,454,923 B1 * | 9/2002 | Dodgson et al. ............ 204/415 |
| 6,500,574 B1 | 12/2002 | Keegan ........................ 429/23 |
| 6,539,311 B1 * | 3/2003 | Berger ......................... 702/23 |
| 2002/0051898 A1 * | 5/2002 | Moulthrop, Jr. et al. |
| 2002/0110713 A1 * | 8/2002 | Reindl et al. |

\* cited by examiner

*Primary Examiner*—Patrick Assouad
*Assistant Examiner*—Mary Catherine Baran
(74) *Attorney, Agent, or Firm*—Cantor Colburn LLP (57) ABSTRACT

A method of monitoring the operation of a gas sensor is disclosed. A system signal is provided in response to sensing first or second system conditions, and a gas concentration signal is provided in response to sensing first or second gas concentration levels of a gas. In response to the system and gas concentration signals, a signal indicating the operating condition of the gas sensor is provided.

24 Claims, 5 Drawing Sheets

| 320 | | Fluid Flow Signal 350 | |
|---|---|---|---|
| | | Flow | No Flow |
| Sensor | Expected | Ok | Ok |
| | Not Expected | Check | Check |

METHOD OF MONITORING THE OPERATION OF GAS SENSOR AND SYSTEM THEREFOR

BACKGROUND OF THE INVENTION

The present disclosure relates generally to a method of monitoring the operation of a gas sensor, and particularly to a method of monitoring the operation of a hydrogen sensor in an electrochemical cell system.

Electrochemical cell systems may employ electrolysis modules in combination with fuel cell modules, thereby enabling the fuel cell module to receive hydrogen fuel from the electrolysis module, either directly or through an intermediate hydrogen storage device. The generation of hydrogen fuel from the electrolysis module also typically results in byproduct water, which is sent through a phase separator to separate saturated hydrogen gas from the water. However, typically some saturated hydrogen remains entrained in the water, which is subsequently stored in a water storage device during a purge process. At the water storage device, the entrained hydrogen may evaporate out of the water and become captured within the interior of the water storage device, thereby increasing the concentration of hydrogen gas at that location. Hydrogen concentrations in excess of about 1000 parts per million (ppm) are undesirable, and in excess of about 4000 ppm may be explosive. Accordingly, hydrogen sensors are used to monitor the concentration levels of hydrogen present, and since hydrogen is a combustible gas, more than one sensor may be employed. Since the system cost is effected by the application of redundant components, it would be advantageous to have an intelligent system that does not rely on redundant components.

SUMMARY OF THE INVENTION

In one embodiment, a method of monitoring the operation of a gas sensor is disclosed. A system signal is provided in response to sensing first or second system conditions, and a gas concentration signal is provided in response to sensing first or second gas concentration levels of a gas. In response to the system and gas concentration signals, a signal indicating the operating condition of the gas sensor is provided.

In another embodiment, an electrochemical cell system having an electrolysis module that receives water and electricity and generates hydrogen in response thereto is disclosed. A phase separator in fluid communication with the electrolysis module separates hydrogen gas and water. The water is subsequently stored at a water storage device. A fluid flow determining arrangement is in fluid communication with the water storage device for sensing the flow of water to the water storage device, and a hydrogen gas sensor is in fluid communication with the water storage device for sensing the concentration of hydrogen gas evaporating from the stored water. A monitoring system, in signal communication with the fluid flow determining arrangement and the hydrogen gas sensor, is adapted to provide an OK signal and a Check Sensor signal for the hydrogen gas sensor in response to signals received from the fluid flow determining arrangement and the hydrogen gas sensor.

In a further embodiment, a monitoring system for an electrochemical cell system includes means for sensing water flow to a water storage device of the electrochemical cell system, means for sensing the concentration of hydrogen gas at the water storage device, and means for signaling the condition of the hydrogen gas sensing means at the water storage device in response to the water flow sensing means and the hydrogen gas sensing means.

In yet another embodiment, a monitoring system for an electrochemical cell system includes a processor programmed to receive a signal from a first sensor representative of the flow of water to a water storage device, receive a signal from a second sensor representative of the concentration of hydrogen gas at the water storage device, process the water flow signal and the hydrogen gas signal according to a transfer function, and provide a signal representative of the operating condition of the second sensor in response thereto.

BRIEF DESCRIPTION OF THE DRAWINGS

Referring to the exemplary drawings wherein like elements are numbered alike in the accompanying Figures.

DETAILED DESCRIPTION OF THE INVENTION

Figure 1:
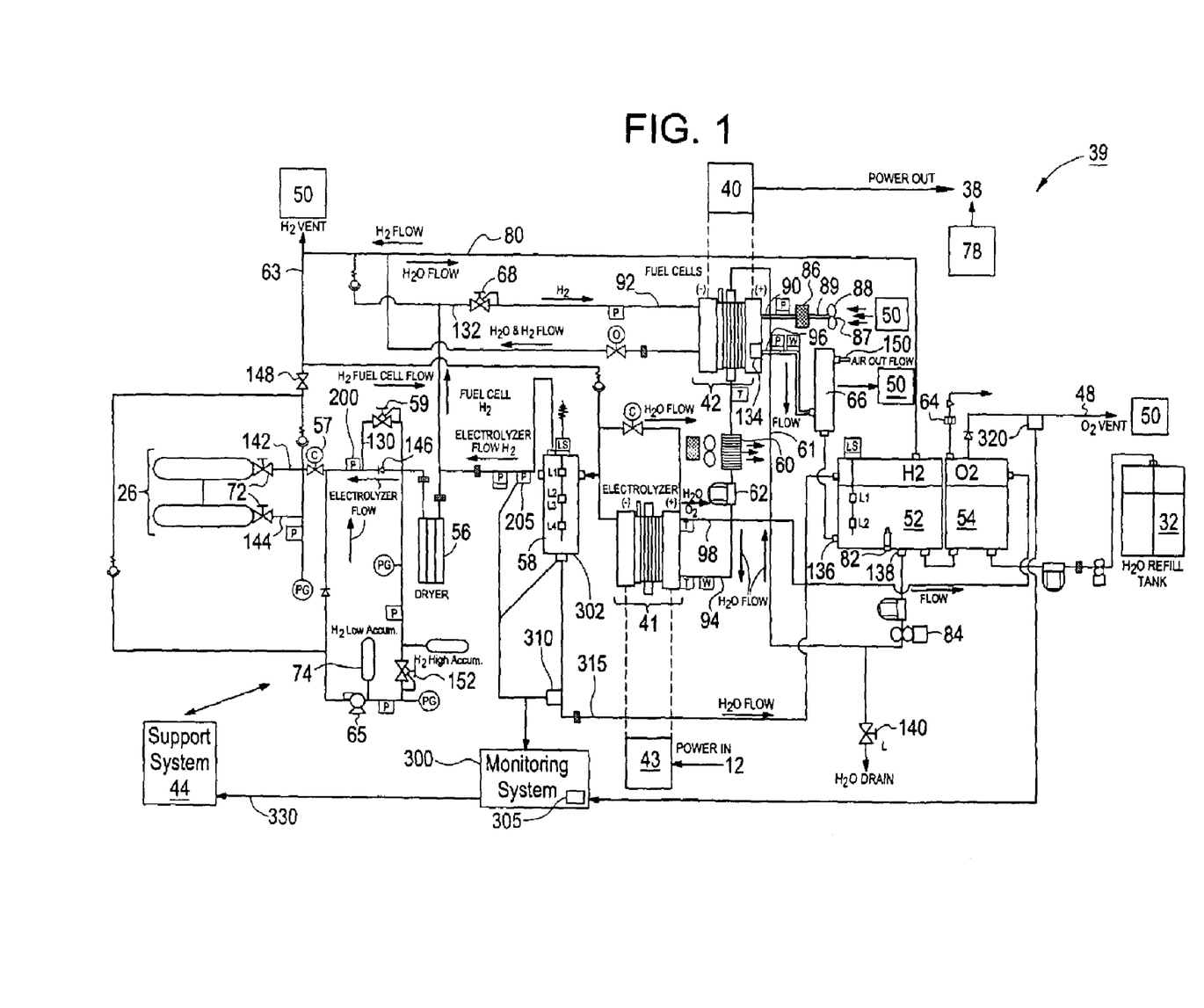
FIG. 1 is an exemplary block diagram of a regenerative electrochemical cell system for implementing an embodiment of the invention.

FIG. 1 is an exemplary block diagram representing a regenerative electrochemical cell (regen-system) 39, which includes an electrolysis module (or stack) 41 in fluid communication with an oxygen-releasing vent 48 that fluidly communicates with the surrounding atmosphere 50. Optionally disposed between the electrolysis module 41 and the oxygen vent 48 is a water storage device 52, 54, which is in fluid communication with the cathode chamber of the electrolysis module 41. Also, hydrogen storage device 26 is in fluid communication with the electrolysis module 41, with an optional phase separation device 58 disposed therebetween. The hydrogen storage device 26 is further in fluid communication with the fuel cell module 42, preferably via optional dryer 56. Meanwhile, the fuel cell module 42 is in fluid communication with the surrounding atmosphere 50 via oxygen/water phase separation device 66, and via water storage device 52, 54 and oxygen vent 48. In addition, the fuel cell module 42 is in electrical communication with a power load 38 via a power conditioner 40, and optionally in electrical communication with a bridge power device 78, which is also in electrical communication with the power load 38. Electrolysis module 41 is in electrical communication with the renewable power source 12, via power conditioner 43. Optionally, the bridge power device 78 is integrated with the renewable power source 12 as a single device. An optional backup water storage device 32 is provided in fluid communication with water storage device 52, 54.

Figure 2:
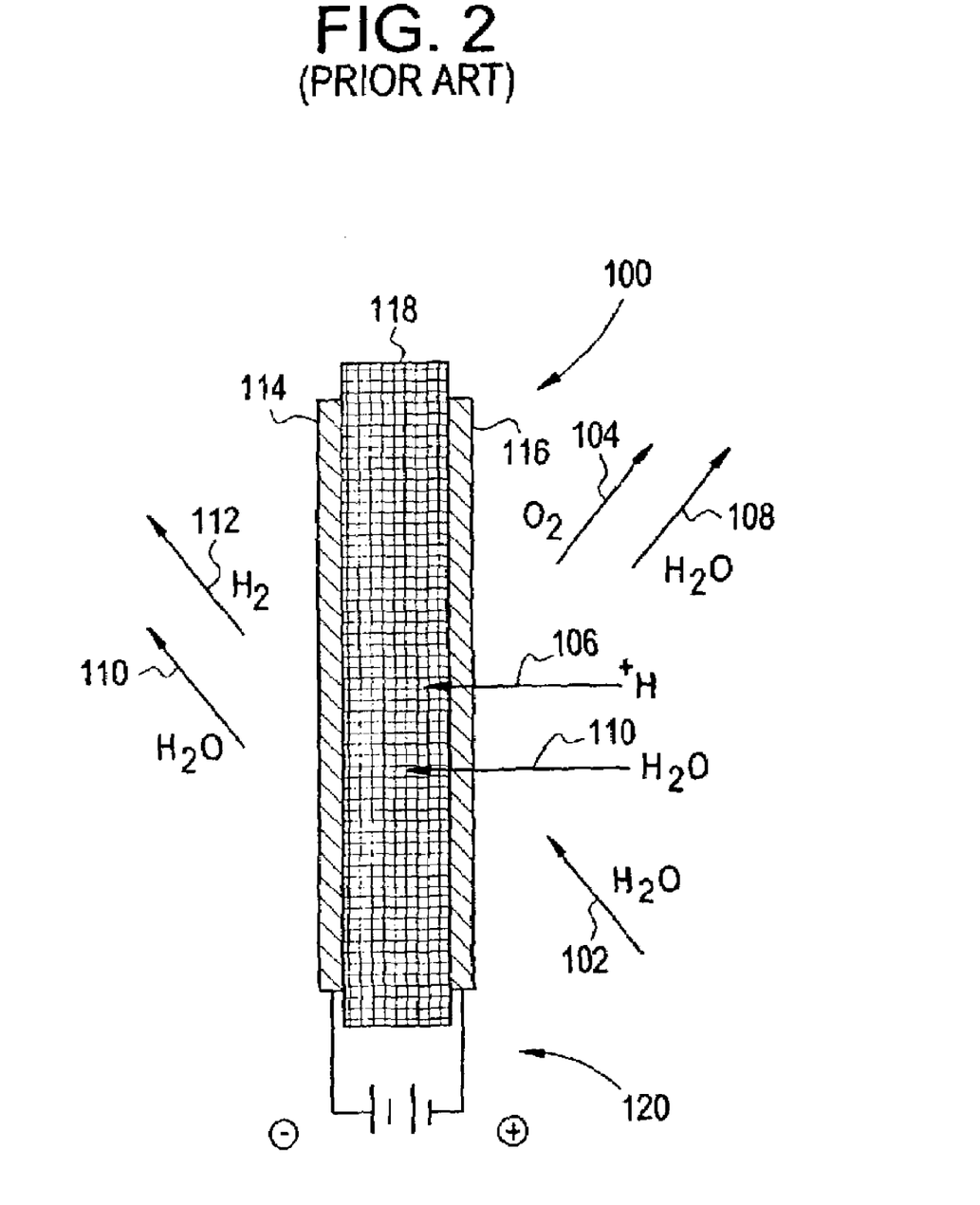
FIG. 2 is a schematic diagram illustrating a prior art electrochemical cell for use in the system of FIG. 1.

The electrolysis module 41 can have any desired number of electrolysis cells 100, depicted in FIG. 2, depending upon the desired rate of hydrogen production. Each electrolysis cell 100 includes an electrolyte, depicted as 118, disposed between, and in ionic communication with, electrodes 114, 116. One of the electrodes 116 is in fluid communication with a water source (e.g., 52, 54, 32, a continuous water supply, or the like), while the other electrode 114 is in fluid communication with the fuel cell module 42, preferably via a phase separation device 58 and the hydrogen storage device 26.

The water storage device 52, 54 contains a water intake port 136 and a water output port 138. The water intake port 136 is in fluid communication with fuel cell module 42 and the output port 138 is in fluid communication with a water pump 84 that is in fluid communication with the electrolysis module 41. Depending upon the design of the water storage device 52, 54, a single tank can be employed to recover water from the hydrogen and the oxygen outlets from the fuel cell module 42, or separate water storage devices (e.g., 52, 54) can be employed. Furthermore, depending upon the availability of make-up water for the regen-system 39, the backup water storage device 32 may also be employed. Alternatively, or in addition, the water storage device 52, 54 can optionally be in fluid communication with a continuous water source (e.g., a lake, a river, a municipal water supply, and the like, as well as combinations comprising at least one of the foregoing water sources).

Additionally, the water system (i.e., the water storage device(s), and fluid communication conduits) may comprise a heating system 82 to increase the temperature of the water, thereby reducing fuel cell startup time. This heating system 82 may include resistance heaters within and/or around the piping system and/or within the water storage devices (e.g., heater 82 as shown in water storage device 52, 54). The heating system 82, alternatively, may constitute both a heating system component and a plumbing system component, such as a tube heater that serves the dual function of being a piping connection. Alternately, the heater 82 may be incorporated in an element of the fuel cell module 42 or the electrolysis module 41 in the form of an integrated component with the heating element forming part of an end plate or fluid communication section of the module. Alternatively, the heating method may utilize a radiant heating method such as an infrared source within the system or externally located. These heaters 82 may be in the form of a mat, a tube, a coil, a rod style heater, and others, as well as combinations comprising at least one of these heaters. Alternately, the heater 82 may be part of a thermal management or hydration sub-system whose fluid may be other than water based.

The heating system 82 may further comprise freeze protection, as part of the above-described system or via additional components. Freeze protection can be attained by employing various insulative measures to minimize heat loss, isolation valves 140 that allow draining of water from non-freeze tolerant components of the regen-system 39, such as water pump(s) 84, and the like. Alternately, continuous water flow may be utilized with the heating system 82, and/or the heating system 82 may utilize parasitic loads (e.g., heat generated by the water pump, control system electronics, and the like) to create the heat energy and prevent water freezing during low ambient temperature operation (e.g., −30° F. (degrees Fahrenheit)). The use of parasitic heat can be employed in combination with various controls in support system 44, such as a temperature sensor, and the like, such that the pump 84 may be operated continuously, or the pump 84 can be operated intermittently based upon factors such as the actual water temperature.

Water pump 84, in fluid communication with both the water storage device 52, 54 and the electrolysis module 41, can optionally allow two-way water flow. Therefore, during electrolysis module 41 recharge operations, water pump 84 can allow excess water that accumulates in the regen-system 39 to flow into water storage device 52, 54, preventing flooding of the regen-system 39. This pump 84, which can be in fluid communication with the electrolysis module 41 via the fuel cell module 42, is preferably capable of discharging the desired water to the electrolysis module 41 at a pressure to enable efficient regen-system operation. For example, the water pump 84 is preferably capable of discharging water to the electrolysis module 41 at a pressure up to and exceeding about 2.1 megaPascals (MPa) (300 pounds per square inch (psi)) during fuel cell module 42 operation.

As with the water storage device 52, 54 and the water pump 84, the hydrogen storage device 26 is in fluid communication with the electrolysis module 41. The hydrogen storage device 26 comprises a hydrogen gas intake port 142 and a hydrogen gas output port 144. The hydrogen gas intake port 142 is in fluid communication with electrolysis module 41, while the hydrogen gas output port 144 is in fluid communication with the fuel cell module 42.

Within the hydrogen storage device 26, the hydrogen may be stored at various pressures, depending upon the hydrogen storage device 26 design and the storage needs of the regen-system 39. Preferably, the hydrogen storage device 26 is a pressurized device suitable to store hydrogen gas at pressures of up to, or exceeding, about 1,000 pounds per square inch (psi), with the capability of storing hydrogen gas at pressures of up to, or exceeding, about 2,000 psi preferred and about 10,000 psi more preferred.

The desired hydrogen storage pressure may be achieved through the use of the electrolysis module 41 alone or in concert with a pressure boosting system (e.g., a compressor 65) within the regen-system 39. Alternatively, or in addition, the hydrogen storage device 26 may include mechanical or other pressure increasing methods, such as metal hydride pumping or proton exchange membrane (PEM) based pumping systems for example. The pumping system may use a single stage or multiple stages to achieve the desired final compression level. The compression process may be used in various combinations or quantities to achieve the required compression within the system.

In an alternative to employing pressurized hydrogen storage device(s) 26, other techniques of storing hydrogen can be employed; e.g., hydrogen can be stored in the form of a gas, solid, or liquid. For example, if a non-pressurized device is employed the hydrogen can be stored as a solid, e.g., as a metal hydride, in a carbon based storage (e.g., particulates, nanofibers, nanotubes, or the like), and others, as well as combinations comprising at least one of the foregoing hydrogen storage forms.

Hydrogen storage device 26 can be formed of any material capable of withstanding the desired pressures. Some possible materials include ferrous materials (such as steel, e.g., stainless steel, and the like) titanium, carbon (e.g., woven carbon fiber materials, and the like), plastics, any other comparable high-strength materials, as well as composites, alloys, and mixtures comprising at least one of the foregoing materials Furthermore, the hydrogen storage device 26 may be lined with sealant(s), surface finish(es), coatings, or the like, to prevent corrosion or other tank material-related contamination from communicating with the hydrogen or any condensate in the device, and to prevent the contamination of regen-system components.

Hydrogen gas drying techniques may also be employed as part of the hydrogen storage system. These drying systems 56 may include, for example, desiccant based drying schemes (e.g., a swing bed adsorber, and other desiccant based absorbers), phase separators, membrane drying systems (e.g., palladium diffusers, and the like), coalescing filters, condensing systems (e.g., utilizing thermal electric cooler, vortex tube coolers, vapor or air cycle refrigeration system, and the like), and the like, as well as combinations comprising at least one of the foregoing drying systems.

Optionally, the hydrogen storage system 26 can comprise an inverted hydrogen storage device (i.e., a hydrogen storage device comprising a bi-directional opening (inlet and outlet), and/or which allows hydrogen removal from an upper vessel connection, while water is removed via a gravity drain port (not shown). In the inverted hydrogen storage device, the device is allowed to collect condensed moisture and return this condensed liquid to the water storage device 52, 54 or other water sub-system components. Alternatively, the inverted hydrogen storage device 26 can be used as a secondary water separator when used with a primary water separator, e.g., hydrogen/water phase separation device 58 (which may comprise multiple stages of separators to improve water extraction and recovery). Employing the inverted hydrogen storage device eliminates the need for a dryer 56 and associated hardware. Further eliminated is the need for a compressor 65 if the electrolysis module 41 is operated to produce hydrogen at a desired storage pressure.

In fluid communication with the hydrogen storage device 26 are optional dryer(s) 56, and the fuel cell module 42. The dryer 56 can comprise any device capable of removing water vapor from the hydrogen stream, as discussed above. Some water is removed from the saturated hydrogen stream at the phase separation device 58. Saturated hydrogen gas from the phase separation device 58 then flows into dryer 56 (having a lower water saturation than the feed stream to phase separation device 56). In an embodiment, the dryer 56 includes a bed of a moisture absorbent (and/or adsorbent) material, i.e., a desiccant. As the saturated hydrogen gas flows into the dryer 56, water with trace amounts of hydrogen entrained therein is removed and subsequently returned to the water source, or water storage device 52, 54, through a low-pressure hydrogen separator 74. Low pressure hydrogen separator 74 allows hydrogen gas to escape from the water stream due to the reduced pressure, and also recycles water to electrolysis module 41 at a lower pressure than the water exiting the phase separation device 58. Alternatively, a diffuser 146 may be provided in addition to the dryer 56, with a one-way check valve 72 preferably disposed between the hydrogen storage device 26 and the dryer 56 to prevent high-pressure backflow of the hydrogen gas.

Although the dryer 56 is preferably sized to hold all moisture generated during electrolysis based on the size of the hydrogen storage system, the dryer 56 has limited capacity for water removal. The dryer 56 is therefore preferably periodically purged to remove accumulated moisture. Purging the dryer 56 is accomplished by flowing stored hydrogen gas from the hydrogen storage device 26 through the dryer bed of dryer 56. As the hydrogen gas from hydrogen storage device 26 flows through the dryer 56, the dryer bed is purged of its moisture. A first pressure regulator 59 is fluidly connected between the storage hydrogen storage device 26 and the dryer 56. The pressure regulator 59 reduces the gas pressure from the hydrogen storage device 26 to provide an efficient and low cost solution for purging the dryer 56. The use of the first pressure regulator 59 minimizes the amounts of hydrogen gas vented (lost) to the atmosphere and provides a more efficient process for bed desorption Moreover, the use of the first pressure regulator 59 prevents high-pressure gas exposure to the phase separator 58 from hydrogen storage device 26. The pressure regulator 59 is preferably set at or about the operating pressure for the fuel cell module 42. More preferably, the pressure is set a few pounds per square inch greater than the operating pressure for the fuel cell module 42. Preferably, the pressure regulator 59 is set at a pressure of less than or equal to about 14 psi greater than the fuel cell operating pressure, with a pressure of less than or equal to about 7 psi more preferred. Also preferred is a pressure of greater than or equal to about 2 psi greater than the fuel cell operating pressure, with a pressure of greater than or equal to about 3 psi more preferred.

The purging process comprises passing the reduced pressure hydrogen through the dryer 56 and desorbing the previously absorbed (and adsorbed) water from the dryer 56. The now hydrated hydrogen can either be vented to the atmosphere 50, and/or all or a portion of the hydrated hydrogen can preferably be directed to the fuel cell module 42 for consumption and possibly subsequent water recovery. Preferably, the dryer 56 acts as a hydrogen humidification device to inhibit fuel cell electrolyte dry-out. Alternatively, the vented hydrated hydrogen may be consumed in a combustion or a catalytic burner (not shown), or the like.

The fuel cell module 42 is used to generate energy during a power generation mode. During the power generation mode, a control valve 148 is actuated (and preferably left open while in idle mode), and hydrogen gas flows from the hydrogen storage device 26 to the fuel cell module 42. Hydrogen gas electrochemically reacts with oxygen ($O_2$) in the fuel cell module 42 to release energy and form by-product water. This water is preferably retained in the regen-system 39. The oxygen gas can be either stored as pressurized gas or supplied from ambient air. A second pressure regulator 68 is fluidly connected to an inlet 92 of the fuel cell module 42. The second pressure regulator 68 is set at the optimal operating pressure of the fuel cell module 42. Preferably, the second pressure regulator 68 is set at about 40 psi. The second pressure regulator 68 protects the fuel cell module 42 from the high pressures obtained during hydrogen gas generation (pressures up to and exceeding about 4,000 psi) and acts as a secondary pressure reducer. The second pressure regulator 68 also serves as a redundant mechanism in the event of a check valve 72 fault or leak.

As previously discussed, the first pressure regulator 59 is preferably set at a pressure rating above the rating for second pressure regulator 68 (e.g., a few psi greater than the pressure rating for regulator 68). Under these conditions, the first pressure regulator 59 can function as a backup to second pressure regulator 68 in the event of a "wide open" fault of regulator 68. Moreover, since the first pressure regulator 59 is set at a value greater than the second pressure regulator 68, pressure is continuously maintained to the fuel cell module 42, even during electrolysis. Since it is preferred not to employ shutoff or multi-way valves that need to be actuated between the hydrogen storage device 26 and fuel cell module 42, the fuel cell module 42 is always ready to operate. A shutoff valve 57, normally disposed between the hydrogen storage device 26 and the dryer 56, is open when the regen-system 39 is operational, and is typically only closed for system faults or system shutoff. As a result, the switching delays caused by valve actuation are eliminated as the regen-system 39 cycles between the charging/storage mode (e.g., hydrogen generation) and the power generation mode. During the power generation mode, the use of first pressure regulator 59 causes a low pressure purging gas to flow into dryer 56 and desorb the bed of accumulated moisture. This permits the regen-system 39 to employ a lower cost phase separation device 58 and to optionally eliminate check valves at separator outlet. Use of the lower pressure operated phase separation device 58 is particularly preferred when the regen-system 39 employs a hydrogen pressure boosting system (e.g., a compressor 65 or the like), due to its low cost.

From the dryer 56, hydrogen gas flows to the fuel cell module 42. The fuel cell module 42 includes any desired number of fuel cells 100, based upon the desired power supply capabilities of the regen-system 39. Each fuel cell 100 within the fuel cell module 42 has an electrolyte, depicted as 118, disposed between, and in ionic communication with, two electrodes 114, 116. One electrode 114 is in fluid communication with a hydrogen supply (e.g., hydrogen storage device 26 and/or electrolysis module 41), while the other electrode 116 is in fluid communication with an oxygen supply (e.g., the surrounding atmosphere 50, the gaseous phase of the water storage device 52, the gaseous phase of the oxygen/water phase separation device 66, and/or an oxygen storage device (not shown)).

If the fuel cell module 42 is in fluid communication with the surrounding atmosphere 50, reduction of any pressure differentials between the fuel cell module 42 and the surrounding atmosphere 50, as well as uptake of air from the surrounding atmosphere 50, and filtering of the air, can be accomplished by various methods, including, for example, using an air compressor(s), depicted generally at 88, fan(s), also depicted generally at 88, filter(s) 86, and the like, as well as combinations comprising at least one of the foregoing methods. For example, the air compressor 88 contains an air intake port 87 and an air output port 89. The output port 89 is in fluid communication with fuel cell module 42 and the intake port 87 is in fluid communication with the surrounding atmosphere 50. Air compressor 88 draws air from the surrounding atmosphere 50, compresses it, and then sends it to fuel cell module 42. The generation of compressed air by air compressor 88 facilitates air uptake by fuel cell module 42.

In electrical communication with the fuel cell module 42 is a power load 38. The power load 38 can be a direct current (DC) load or an alternating current (AC) load and can include residential and commercial loads and the like (including batteries for alternatively powering those power loads), with the electricity from the fuel cell module 42 appropriately conditioned by power conditioner 40. Furthermore, the regen-system 39 can be connected directly to the power load 38 with sensors, via support system 44, capable of drawing power upon various conditions, for example, cease of grid power flow, increased power demand over a predetermined amount, operation for system testing, commands from centralized or distributed control systems (e.g., connected via various methods including wireless, wired (e.g., modem, and the like)), infrared and radio frequency commands, and the like, as well as combinations comprising at least one of the foregoing command systems. These command systems may further include operations devices in operable communication with the regen-system, such as communication devices and control devices. Possible operations devices include processing units (e.g., computers, and the like) and similar equipment. Communication between the command systems and the regen-system 39 may be accomplished via support system 44.

In contrast to the fuel cell module 42, the electrolysis module 41 is connected to a renewable power source 12. The renewable power source 12 can be any device capable of providing sufficient power to the electrolysis module 41 to enable the desired hydrogen production rate. Some possible renewable power sources 12 include grid power, battery, solar power, hydroelectric power, tidal power, wind power, and the like, as well as combinations comprising at least one of the foregoing power sources (e.g., via solar panel(s), wind mill(s), dams with turbines, and the like).

The renewable power source 12 can introduce either AC or DC power to the regen-system 39, preferably via a power conditioner 43. The power conditioner 43 may provide control of the energy source, e.g., current control, voltage control, switch control, as well as combinations of these controls, and the like. The power conditioner 43, and/or a control system (not shown), can monitor voltage, current, or both, in order to control the power from the power conditioner 43.

In addition to the power that passes out of the regen-system 39 via the power conditioner 40, heat energy may be recovered from the regen-system 39 with a heat exchanger 60 and/or radiator 61. The heat exchanger 60 can be disposed in fluid communication with both the fuel cell module 42 and the electrolysis module 41 such that the heat produced in the electrolysis module 41 can be employed to heat the fuel cell module 42. Alternatively, or in addition, the heat exchanger 60 and/or radiator 61 can be in thermal communication with the surrounding environment 50, or can be directed to a thermal load; e.g., a building (such as an office building(s), house(s), shopping center, and the like).

In addition to the above equipment, the regen-system 39 may further comprise various other equipment, such as valves (e.g., relief valves, check valves, manual valves, actuated valves, needle valves, and the like, as well as combinations comprising at least one of the foregoing valves), filters (e.g., deionization bed cartridge(s), filter cartridge(s), and the like, as well as combinations comprising at least one of the foregoing filters), sensors (e.g., pressure, temperature, flow, conductivity, gas mixture, water level, and the like, as well as combinations comprising at least one of the foregoing sensors), controls (e.g., temperature (such heaters, heat exchangers, coolers, dryers, and the like), pressure (such as, compressors, and the like), flow (such as, pumps, fans, blowers, and the like), power, and the like, as well as combinations comprising at least one of the foregoing controls), conduits (e.g., fluid conduits, electrical conduits, and the like), and the like, as well as combinations comprising at least one of the foregoing equipment. It should be noted that, depending upon regen-system location (remote, metropolitan, industrial, and the like), its specific function (e.g., front line electrical production, backup production), and the criticality of the source that the regen-system is backing-up, redundant components or merely additional components can be employed, in parallel or series operation. For example, water storage devices, dryers, heat exchanger, radiators, deionization beds, filters, phase separation devices, and the like.

In fluid communication with and between phase separation device 58 and water storage device 52, 54 is a flow solenoid 302, which opens and closes under the command of support system 44 to control the flow of water to water storage device 52, 54. A hydrogen pressure sensor 205 in fluid communication with the hydrogen gas from phase separation device 58 provides change-of-pressure information to a monitoring system 300. In an embodiment, the presence of water flow from phase separation device 58 to water storage device 52, 54 is inferred from the command signal sent to flow solenoid 302 and from the signal received from pressure sensor 205. In response to an operating condition where an OPEN command signal is sent to flow solenoid 302 and a change-of-pressure signal is received from pressure sensor 205, monitoring system 300, or optionally support system 44, infers that water is flowing from phase separation device 58 to water storage device 52, 54. The inferred fluid flow condition resulting from the combination of solenoid OPEN command at flow solenoid 302 and the change-of-pressure signal at pressure sensor 205 is herein referred to as a fluid flow signal, or more generally as a system signal. The combination of flow solenoid 302 and pressure sensor 205 is exemplary only of fluid flow determining arrangement, and other arrangements may equally be applicable.

Optionally, in fluid communication with and between phase separation device 58 and water storage device 52, 54 is a flow sensor 310, which monitors the flow of water in flow line 315, and communicates the flow condition to a monitoring system 300. Flow sensor 310 may be a mass flow sensing device, a fluid pressure sensing device, or any other sensing device suitable for sensing flow in flow line 315. The signal from flow sensor 310 is also herein referred to as a fluid flow signal, or more generally as a system signal. The fluid flow signal (or system signal) from optional flow sensor 310 provides similar fluid flow information as does the fluid flow signal (or system signal) from the combination of solenoid OPEN command at flow solenoid 302 and the change-of-pressure signal at pressure sensor 205 discussed above. Accordingly, the artisan will appreciate that an arrangement employing flow sensor 310 is interchangeable with an arrangement employing alternative flow sensing arrangements, such as the combination of solenoid OPEN command at flow solenoid 302 and the change-of-pressure signal at pressure sensor 205, for example.

In fluid communication with water storage device 52, 54 is a hydrogen sensor 320, which monitors the level of hydrogen gas present in the air mixture as it evaporates out of the water in water storage device 52, 54. Monitoring system 300 is in signal communication with support system 44 to provide information relating to the operating conditions of regen-system 39, and specifically to provide information relating to the signals from flow sensor 310 and hydrogen sensor 320. Monitoring system 300 includes a processor 305 that is programmed for carrying out the signal processing. In an embodiment, monitoring system 300 may be integral with support system 44.

During normal operation of regen-system 39, hydrogen sensor 320 reads about 1% to about 4% LFL (Lower Flammability Limit) (a second nominal hydrogen level), which is an indication of the amount of hydrogen gas present in the gas mixture within water storage device 52, 54. Depending on system, regen-system 39 may operate at a normal LFL of about 1%, however, a normal reading of about 3% provides a more distinguishable reading for performing health monitoring on sensor 320, as will be discussed below. During a purge process where the excess water in phase separator 58 drains to water storage device 52, 54, saturated hydrogen gas flowing to water storage device 52, 54 results in a rapid change in the concentration of hydrogen gas as it evaporates out of the water, which is sensed by hydrogen sensor 320. During this purge process, hydrogen sensor 320 momentarily reads from about 7% LFL to about 10% LFL, with a range from about 9% to about 10% LFL being typical (a first nominal hydrogen level). At about 100% LFL, or at about 4000 ppm (parts per million) of hydrogen gas concentration, an explosive condition may be present. At about 25% LFL, or at about 1000 ppm of hydrogen gas concentration, support system 44 preferably commands regen-system 39 to shut down. By monitoring the reading of hydrogen sensor 320, an explosive condition may be avoided, and by monitoring the health of hydrogen sensor 320, use of redundant sensors may be avoided.

While an exemplary embodiment depicts a hydrogen concentration level of about 1% to about 4% LFL as being a second nominal hydrogen level in the absence of water flow to water storage device 52, 54 (a second system condition), and a hydrogen concentration level of about 7% to about 10% LFL as being a first nominal hydrogen level in the presence of water flow to water storage device 52, 54 (a first system condition), the artisan will appreciate that other hydrogen concentration levels may be applicable for the first and second nominal hydrogen levels without departing from the scope of the invention. Additionally, while an exemplary embodiment depicts the presence and absence of water flow to water storage device 52, 54 as being first and second system conditions, the artisan will appreciate that other system conditions, such as first and second component temperatures for example, may be applicable for the first and second system conditions without departing from the scope of the invention. Accordingly, regen-system 39 and the method of operation thereof preferably includes a determination of first and second nominal hydrogen concentration levels at first and second system conditions, respectively.

Figure 3:
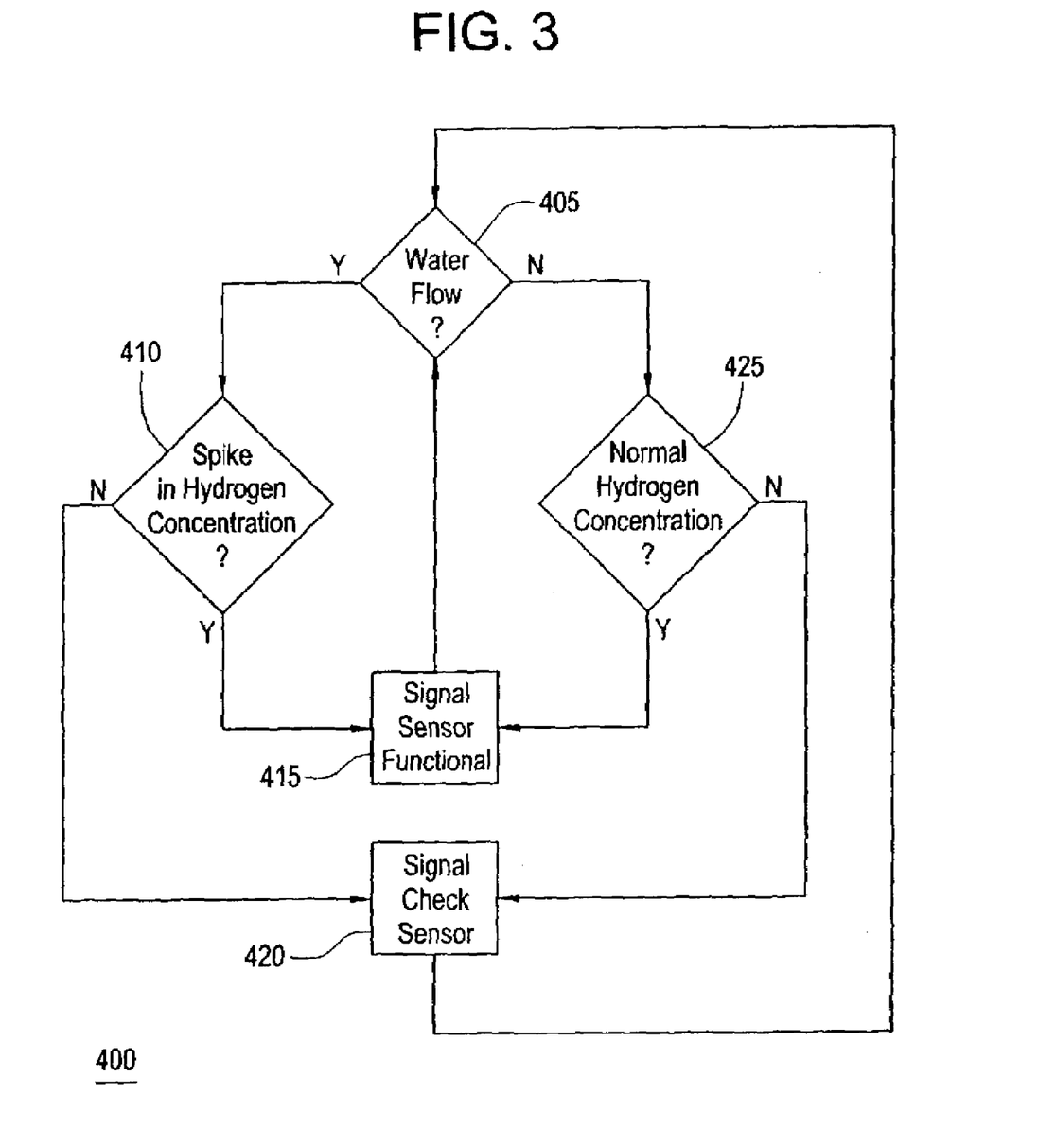
FIG. 3 is an exemplary method in accordance with an embodiment of the invention.

FIG. 3 depicts a continuous method 400 for using the information from sensors 310 and 320 to monitor the health of hydrogen sensor 320. As discussed above, an alternative embodiment may employ the fluid flow signal from the combination of solenoid OPEN command at flow solenoid 302 and the change-of-pressure signal at pressure sensor 205 in place of the fluid flow signal from sensor 310. At block 405, monitoring system 300 reads flow sensor 310 to determine if water is flowing in flow line 315. If yes, monitoring system 300 reads hydrogen sensor 320 to determine 410 if a signature spike in hydrogen gas concentration is present. If yes, monitoring system 300 signals 415 that hydrogen sensor 320 is functioning as expected. If the outcome of block 410 is no, then monitoring system 300 signals 420 that hydrogen sensor 320 is not functioning as expected and should be checked. If the outcome of block 405 is no (phase separator 58 is not purging), monitoring system 300 reads hydrogen sensor 320 to determine 425 if it is reading a normal percentage LFL (about 1% to about 4% LFL). If yes, the logic of monitoring system 300 proceeds to block 415 and provides the functional signal as discussed above. If no, the logic of monitoring system 300 proceeds to block 420 and provides the check-sensor signal as discussed above. Upon completion of the logical processes within blocks 415 and 420, the logic of monitoring system 300 returns to block 405 where the sensor-health monitoring cycle repeats until terminated by other system controls via support system 44.

Figure 4:
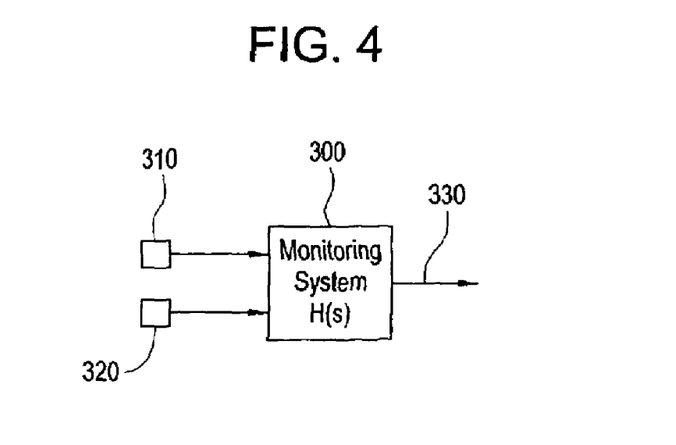
FIG. 4 is an exemplary block diagram of a monitoring system for implementing the method of FIG. 3.
Figure 5:
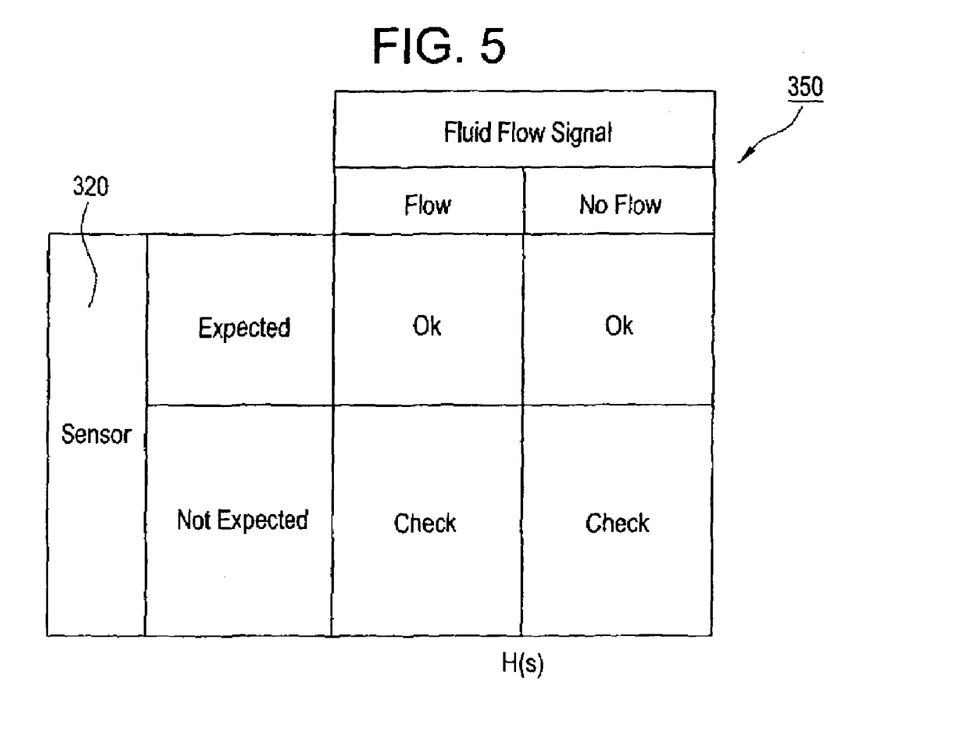
FIG. 5 is an alternative method to the method of FIG. 3.
Figure 6:
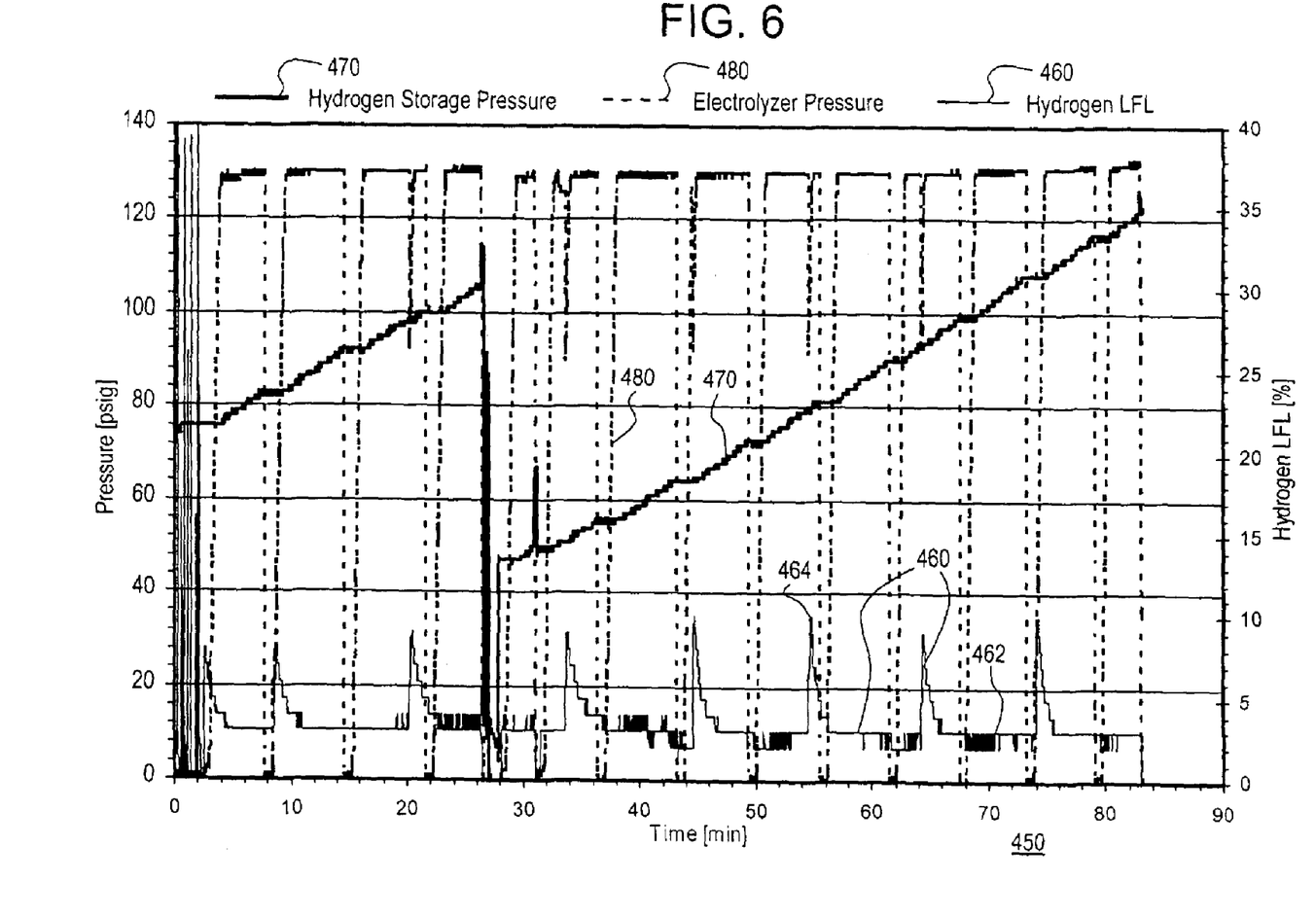
FIG. 6 is a graphical representation of a response from a system implementing an embodiment of the invention.

FIG. 4 depicts the signal flow through monitoring system 300, which receives signal information from flow sensor 310 and hydrogen sensor 320 and applies a transfer function H(s) to generate an output signal 330 for subsequent processing at support system 44. As discussed above, an alternative embodiment may employ the fluid flow signal from the combination of solenoid OPEN command at flow solenoid 302 and the change-of-pressure signal at pressure sensor 205 in place of the fluid flow signal from sensor 310. Transfer function H(s) may be represented by method 400, as discussed above in reference to FIG. 3, or by the logic table 350 depicted in FIG. 5. In accordance with logic table 350: if flow sensor 310 indicates flow in flow line 315 and hydrogen sensor 320 indicates an expected reading (spike in hydrogen concentration), then monitoring system 300 signals an OK condition for hydrogen sensor 320; if flow sensor 310 indicates no flow and hydrogen sensor 320 indicates an expected reading (reading about 1% to about 4% LFL), then monitoring system 300 signals an OK condition for hydrogen sensor 320; if flow sensor 310 indicates flow and hydrogen sensor 320 indicates a not expected condition (no spike in hydrogen concentration), then monitoring system 300 signals a Check Sensor condition for hydrogen sensor 320; and, if flow sensor 310 indicates no flow and hydrogen sensor 320 indicates a not expected condition (reading other than about 1% to about 4% LFL), then monitoring system 300 signals a Check Sensor condition for hydrogen sensor 320. Monitoring system 300 may also provide a control signal to support system 44 in response to the signals received from flow sensor 310 and hydrogen sensor 320, thereby providing regen-system 39 with additional protective shut-down measures. FIG. 6 depicts test data 450 relating to regen-system 39 and specifically test data 460 relating to hydrogen sensor 320 sensing normal 462 (reading about 1% to about 4% LFL) (a first nominal) and momentary spike 464 (reading about 7% to about 10% LFL) (a second nominal) concentrations of hydrogen gas present in the gas mixture within water storage device 52, 54. Test data 460 depicts hydrogen LFL (%) as a function of time (minutes), test data 470 depicts hydrogen storage tank 26 pressure (psig; pounds per square inch, gauge) as a function of time (minutes), and test data 480 depicts electrolysis module 41 pressure (psig) as a function of time (minutes). Pressure reading test data 470, 480 is taken from pressure sensors 200 and 205 located at hydrogen storage tank 26 and phase separation device 58, respectively, which experience a change in pressure as water is purged from phase separator 58. One or both of these pressure sensors 200, 205 may be used in combination with pressure sensor 320 and a different logic table (not shown), in place of flow sensor 310, pressure sensor 320, and logic table 350. The temporal relationship between a reading at flow sensor 310 and a reading at hydrogen sensor 320 may also be factored into transfer function H(s) 350, thereby providing trend information or information relating to sensor deterioration over time. As can be seen from FIG. 6, the duration of a hydrogen gas spike sensed by hydrogen sensor 320 is on the order of about 2-minutes, and the time period between hydrogen gas spikes is on the order of about 10-minutes. Accordingly, monitoring system 300 should be adapted to monitor the signals from flow sensor 310 and hydrogen sensor 320 at a rate faster than the rate at which the hydrogen sensor signals change, such as at a rate equal to or greater than about 5 readings per minute for example.

Embodiments of the invention provide a regen-system 39 with a method for monitoring not only the operation of regen-system 39 itself, but also the health of hydrogen sensor 320 within regen-system 39.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of monitoring the operation of a gas sensor for an electrochemical cell, comprising:
   sensing at least one of a first and second system condition in the electrochemical cell and providing a system signal representative thereof;
   sensing at least one of a first and second gas concentration level in the electrochemical cell and providing a gas concentration signal representative thereof; and
   signaling an operating condition of the gas sensor in response to the system signal and the gas concentration signal, the operating condition comprising an OK operating condition, a check sensor operating condition, or any combination comprising at least one of the foregoing conditions.

2. The method of claim 1, wherein:
   said sensing at least one of a first and second system condition includes determining at least one of a first and second flow condition of a fluid in fluid communication with a fluid storage device and providing a fluid flow signal; and
   said sensing at least one of a first and second gas concentration level includes sensing a gas concentration level of a gas released from the fluid in the fluid storage device.

3. The method of claim 2, wherein:
   the gas is hydrogen; and
   the fluid is water.

4. The method of claim 3, wherein:
   the determined first flow condition is water flowing to the water storage device;
   the determined second flow condition is an absence of water forcefully flowing to the water storage device;
   the sensed first gas concentration level is a hydrogen concentration at a first nominal hydrogen level; and
   the sensed second gas concentration level is a hydrogen concentration at a second nominal hydrogen level.

5. The method of claim 4, wherein:
   the first nominal hydrogen level is a value greater than or equal to about 7% LFL and less than or equal to about 10% LFL; and
   the second nominal hydrogen level is a value greater than or equal to about 1% LFL and less than or equal to about 4% LFL.

6. The method of claim 2, wherein said signaling comprises:
   evaluating the fluid flow and gas concentration signals in accordance with a transfer function.

7. The method of claim 6, wherein said evaluating the fluid flow and gas concentration signals in accordance with a transfer function further comprises:
   employing at least one of a process flow method and a lookup table method.

8. The method of claim 7, wherein said process flow method comprises:
   determining if fluid is flowing to the fluid storage device;
   if yes, then:
   determining if a momentary increase in gas concentration level occurs at the fluid storage device in response thereto;
   if yes, then signaling that the gas sensor is functioning as expected; and
   if no, then signaling that the gas sensor is not functioning as expected; and
   if no, then:
   determining if a normal gas concentration level is present at the fluid storage device;

if yes, then signaling that the gas sensor is functioning as expected; and if no, then signaling that the gas sensor is not functioning as expected.

9. The method of claim 7, wherein said lookup table method comprises:
evaluating a fluid flow signal to determine if fluid is flowing to a fluid storage device or not;
evaluating a gas sensor signal to determine if the gas concentration level at the fluid storage device is at an expected concentration level or not;
signaling that the gas sensor is functioning as expected in response to the gas sensor sensing an expected gas concentration level in response to at least one of a fluid flow signal and a no fluid flow signal; and
signaling that the gas sensor is not functioning as expected in response to the gas sensor sensing an unexpected gas concentration level in response to at least one of a fluid flow signal and a no fluid flow signal.

10. An electrochemical cell system, comprising:
an electrolysis module for receiving water and electricity and for generating hydrogen in response thereto;
a phase separator in fluid communication with the electrolysis module for separating hydrogen gas and water;
a water storage device in fluid communication with the phase separator for receiving water therefrom;
a fluid flow determining arrangement in fluid communication with the water storage device for sensing the flow of water to the water storage device;
a hydrogen gas sensor in fluid communication with the water storage device for sensing the concentration of hydrogen gas evaporating from the stored water; and
a monitoring system in signal communication with the fluid flow determining arrangement and the hydrogen gas sensor, the monitoring system being adapted to provide an OK signal and a Check Sensor signal for the hydrogen gas sensor in response to signals received from the fluid flow determining arrangement and the hydrogen gas sensor.

11. The system of claim 10, wherein:
the fluid flow determining arrangement is in fluid communication with the phase separator for sensing the flow of water from the phase separator to the water storage device.

12. The system of claim 10, wherein:
the monitoring system is adapted to provide an OK signal for the hydrogen gas sensor in response to at least one of:
the fluid flow determining arrangement signaling water flow to the water storage device and the hydrogen gas sensor signaling a hydrogen gas concentration at a first nominal hydrogen level; and
the fluid flow determining arrangement signaling no water flow to the water storage device and the hydrogen gas sensor signaling a hydrogen gas concentration at a second nominal hydrogen level.

13. The system of claim 12, wherein:
the first nominal hydrogen level is a value greater than or equal to about 7% LFL and less than or equal to about 10% LFL; and
the second nominal hydrogen level is a value greater than or equal to about 1% LFL and less than or equal to about 4% LFL.

14. The system of claim 10, wherein:
the monitoring system is adapted to provide a Check Sensor signal for the hydrogen gas sensor in response to at least one of:
the fluid flow determining arrangement signaling water flow to the water storage device and the hydrogen gas sensor signaling a hydrogen gas concentration of less than a first nominal hydrogen level; and
the fluid flow determining arrangement signaling an absence of water forcefully flowing to the water storage device and the hydrogen gas sensor signaling a hydrogen gas concentration other than a second nominal hydrogen level.

15. The system of claim 14, wherein:
the first nominal hydrogen level is a value greater than or equal to about 7% LFL and less than or equal to about 10% LFL; and
the second nominal hydrogen level is a value greater than or equal to about 1% LFL and less than or equal to about 4% LFL.

16. The system of claim 10, wherein:
the monitoring system is adapted to monitor the signals from the fluid flow determining arrangement and the hydrogen sensor at a rate greater than the rate at which the signal from the hydrogen sensor changes.

17. The system of claim 10, wherein:
the monitoring system is adapted to monitor the signals from the fluid flow determining arrangement and the hydrogen sensor at a rate equal to or greater than about 5 readings per minute.

18. The system of claim 10, wherein:
the monitoring system is adapted to provide a control signal to a support system in response to signals received from the fluid flow determining arrangement and the hydrogen gas sensor.

19. A monitoring system for an electrochemical cell system, comprising:
means for sensing water flow to a water storage device of the electrochemical cell system;
means for sensing the concentration of hydrogen gas at the water storage device; and
means for signaling the condition of the hydrogen gas sensing means at the water storage device in response to the water flow sensing means and the hydrogen gas sensing means.

20. The monitoring system of claim 19, wherein the means for sensing water flow further comprises:
means for sensing water flow from a phase separator of the electrochemical cell system.

21. The monitoring system of claim 19, wherein the means for sensing the concentration of hydrogen gas comprises:
means for sensing concentrations of hydrogen gas equal to or greater than about 1% LFL.

22. The monitoring system of claim 19, wherein the signaling means comprises:
means for evaluating at least one of a transfer function, a process flow, and a lookup table.

23. A monitoring system for an electrochemical cell system, comprising a processor programmed for:
receiving a signal from a first sensor representative of the flow of water to a water storage device;
receiving a signal from a second sensor representative of the concentration of hydrogen gas at the water storage device;

processing the water flow signal and the hydrogen gas signal according to a transfer function; and providing a signal representative of the operating condition of the second sensor.

24. The monitoring system of claim 23, wherein the transfer function represents at least one of a process flow method and a lookup table method.

* * * * *